United States Patent [19]
Cros et al.

[11] Patent Number: 5,849,480
[45] Date of Patent: Dec. 15, 1998

[54] PROCESS AND DEVICE FOR ASSAYING A HAPTEN

[75] Inventors: Philippe Cros; Robin Kurfurst; Nicole Battail, all of Lyons; Nadia Piga, Ecully, all of France

[73] Assignee: Bio Merieux, Marcy L'Etoile, France

[21] Appl. No.: 379,593

[22] PCT Filed: Jun. 10, 1994

[86] PCT No.: PCT/FR94/00689

§ 371 Date: Mar. 16, 1995

§ 102(e) Date: Mar. 16, 1995

[87] PCT Pub. No.: WO94/29723

PCT Pub. Date: Dec. 22, 1994

[30] Foreign Application Priority Data

Jun. 11, 1993 [FR] France .................................. 93/07093

[51] Int. Cl.⁶ .............................. C12Q 1/68; A61L 5/103
[52] U.S. Cl. ................................ 435/6; 435/7.1; 435/7.9; 435/7.92; 435/7.95; 435/961; 435/969; 435/7.93; 435/7.94; 427/2.13
[58] Field of Search ........................ 422/57, 60; 435/7.1, 435/7.9, 7.92–7.95, 961, 6, 969; 436/527, 531, 532, 810; 427/2.11, 2.13

[56] References Cited

U.S. PATENT DOCUMENTS

| 4,921,788 | 5/1990 | Deutsch ....................................... 436/6 |
| 5,063,081 | 11/1991 | Cozzette et al. ............................. 435/6 |
| 5,510,084 | 4/1996 | Cros et al. ................................. 422/104 |
| 5,723,344 | 3/1998 | Mabilat et al. ........................... 436/518 |

FOREIGN PATENT DOCUMENTS

| 0 089 806 | 9/1983 | European Pat. Off. . |
| 0 205 643 | 12/1986 | European Pat. Off. . |
| 0 310 251 | 4/1989 | European Pat. Off. . |
| 0488152 | 6/1992 | European Pat. Off. . |
| 0 524 864 | 1/1993 | European Pat. Off. . |
| 83/03306 | 9/1983 | WIPO . |
| WO 88/04301 | 6/1988 | WIPO . |
| 91/19812 | 12/1991 | WIPO . |

OTHER PUBLICATIONS

"Acridine–and Cholesterol–Deriatized Solid Supports for Improved Synthesis of 3'–Modified Oligonucleotides," *Bioconjugate Chem.*, ol. 2 (1991) pp. 217–225.

B. Froehler et al., "Phosphoramidate Analogues of DNA: Synthesis and Thermal Stability of Heteroduplexes", *Nucleic Acids Research*, vol. 16, No. 11, pp. 4831–4839, 1988.

N. E. Conway et al., "The Covalent Attachment of Multiple Fluorophores to DNA Containing Phosphorothioate Diesters Results in Highly Sensitive Detection of Single–Stranded DNA", *Biconjugate Chem.*, vol. 2, No. 6, pp. 452–457, 1991.

R. L. Letsinger et al., "Cholesteryl–conjugated oligonucleotides: Synthesis, Properties, and Activity as Inhibitors of Replication of Human Immunodeficiency Virus to Cell Culture", *Proc. Natl. Acad. Sci. USA*, vol. 86, pp. 6553–6556, 1989.

P. Cros et al., "Monoclonal Antibodies to Alpha–Deoxyribonucleotides, Characterisation and Application in PCR Detection", NAMA Conference, Poster 4–37.

F. Kohen et al., eds, "Preparation of Antigenic Steroid–Protein Conjugates," Proceedings of the Fifth Tenovus Workshop, *Steroid Immunoassay*, Apr. 1974, pp. 11–22 and 36–42, 1975.

K. Yamana et al., "Synthesis of Oligonucleotide Deriaties With Pyrene Group At Sugar Fragment", *Tetrahedron Letters*, vol. 32, pp. 6347–6350, 1991.

*Primary Examiner*—James C. Housel
*Assistant Examiner*—Rosemary Ashton
*Attorney, Agent, or Firm*—Oliff & Berridge, PLC

[57] ABSTRACT

A device for assaying haptens includes a solid support linked through a nucleic acid fragment to a reagent that can compete with the hapten for binding to antibodies that bind to the hapten. A process for assaying a hapten uses this device.

38 Claims, 6 Drawing Sheets

PROCESS AND DEVICE FOR ASSAYING A HAPTEN

FIELD OF THE INVENTION

The subject of the present invention is a hapten or anti-hapten antibody assay device and use thereof.

The haptens are small non-immunogenic molecules, that is to say incapable by themselves of promoting an immune reaction by forming antibodies, but which are capable of being recognized by antibodies obtained by immunizing animals under known conditions, in particular by immunization with the hapten-protein conjugate.

BACKGROUND

Various techniques have been proposed for assaying haptens in a sample, among which are the so-called competitive techniques. For example, some authors have described an antigen phase competitive technique in which a hapten, which is identical to the hapten to be assayed, and which is attached to a solid phase, competes with the hapten in the sample for its binding with a labelled specific antibody introduced in a defined quantity. This technique has been described for example for the assay of thyroxine, cortisone and testosterone (see especially Patent Applications EP 089806 and WO 83/03306).

However, because of their small size, it is impossible to adsorb haptens directly onto a solid phase consisting of a polymeric material while retaining the availability towards the binding site of a specific antibody. Thus, in conventional techniques (see especially Clinica Chemica Acta, 162 (1987) 199–206 Elsevier), the hapten is grafted onto a protein or polypeptide ligand for its immobilization onto a solid phase. This technique has, nevertheless, a major disadvantage inherent to the non-immunogenicity of haptens. Indeed, the production of anti-hapten antibodies necessitates the immunization of an animal against haptens coupled to proteins or polypeptides, so as to render them immunogenic, and the anti-hapten antibodies produced in response can interfere, by cross-reactions, with proteins or polypeptides to which the hapten is coupled for its binding onto a solid phase. Moreover, the access of the antibody to the hapten attached onto the support can be obstructed by phenomena of intramolecular reorganization of the proteins or polypeptides under certain physicochemical conditions, which can introduce significant errors in the accuracy of a test.

SUMMARY OF THE INVENTION

Consequently, the subject of the present invention is a support appropriate for the assay of haptens which overcomes the abovementioned disadvantages and which makes it possible, in addition, to control the number of haptens immobilized onto the solid phase and therefore to carry out a real quantitative assay. In addition, the invention provides a support permitting improved orientation of the immobilized haptens and therefore increased accessibility of the latter for their binding with antibodies during the assays.

It has in fact been discovered, surprisingly, that it is possible to overcome the abovementioned disadvantages by using, as attachment intermediate, a nucleic acid fragment.

The subject of the invention is therefore a hapten assay device comprising a solid support and a reagent covalently linked to a ligand to form a conjugate which makes it possible to immobilize the said reagent onto the said solid support, the said reagent being recognized by antibodies capable of recognizing the hapten, characterized by the fact that the said ligand is a nucleic acid fragment.

It is understood that the reagent may be either the hapten to be assayed or a compound having a sufficient immunological analogy with the hapten so that antibodies recognizing one also recognize the other.

The term hapten designates the molecule to be assayed, or an analogue capable of reacting with an antibody specific for the molecule to be assayed.

For example, the haptens may be peptides, glycosylated peptides, metabolytes, vitamins, hormones, prostaglandins, toxins or various medicinal products.

The heptan may be chosen for example from:

a glycosylated peptide such as the N-terminal sequence of the beta subunit of human haemoglobin;

thyroidal hormones especially thyroxine, triiodothyronine; steroidal hormones especially oestrogens such as estriol and estradiol, androgens such as testosterone, progestogens such as progesterone, glucocorticoids such as 11-deoxycorticosterone and cortisone; catecholamines such as adrenaline, noradrenaline, dopamine;

vitamins A, B such as B12, C, D, E and K, folic acid, biotin, thiamine;

nucleosides and nucleotides such as adenosine di- or triphosphate (ADP and ATP), flavine mononucleotide (FMN), nicotinamide adenine dinucleotide (NAD), its phosphate derivative (NADP), thymidine, guanosine and adenosine;

medical products such as digoxin, digitoxigenin, digitoxin, digoxigenin; antibiotics especially aminoglycosides, gentamicin, tobramycin, amikacin, sisomycin, kanamycin, netilmicin, penicillin, tetracycline, terramycin (trade name); or phenobarbital, primidone, ethosuximide, carbamazepine, valproate, theophylline, caffeine, propanolol, procainamide, quinidine, amitriptyline, desipramine, disopyramide and the like;

toxins such as alphatoxin, cholera toxin, staphylococcus enterotoxin B and analogues.

The product resulting from the covalent ligand-reagent coupling is called below "conjugate".

According to one embodiment of the invention, the conjugate is immobilized onto the solid support directly by passive adsorption or covalent attachment of the nucleic acid fragment of the conjugate.

According to another embodiment, the conjugate is immobilized onto the solid support by means of an anti-conjugate, itself immobilized or capable of being immobilized onto the solid support by covalent bonding or by passive adsorption, the anti-conjugate being an agent permitting the immobilization of the conjugate by interaction with the nucleic acid fragment of the conjugate or by interaction with the hapten and with a group present at the junction of the nucleic acid fragment and the hapten.

The anti-conjugate may be for example a second nucleic acid fragment capable of hybridizing with the nucleic acid fragment of the conjugate.

In another embodiment of the invention, the anti-conjugate is an antibody or an antibody fragment directed against the nucleic acid fragment of the conjugate.

According to another embodiment of the invention the anti-conjugate is a protein capable of binding directly or indirectly to the nucleic acid fragment of the conjugate under predetermined conditions.

The nucleic acid fragment is chosen especially from the group consisting of a natural or synthetic DNA or RNA fragment, or a deoxyribonucleotide or a ribonucleotide, or a deoxyribonucleoside or a ribonucleoside. This nucleic acid fragment may be single-stranded, double-stranded, or partially double-stranded. Preferably, a single-stranded fragment is used.

The nucleic acid fragment is an oligodeoxyribonucleotide or an oligoribonucleotide comprising for example 2 to 100 nucleotides, in particular 10 to 50 nucleotides.

The nucleic acid fragment may, in addition, have one or more modified bases or consist only of natural modified bases such as 6-ketopurine, xanthine, 5-methylcytosine, 2-aminopurine, or unnatural modified bases such as thioguanine or 8-oxoguanine. The nucleic acid fragment may have one or more or consist only of nucleosides modified on the glycosidic part, such as carbonucleosides, or have modifications in the phosphodiester skeleton, such as phosphorothioate groups. Likewise, it may have one or more modifications or consist only of nucleosides with alpha or beta anomers or isomers of the D or L series; it being possible for all these elements to be taken independently or in combination.

The term "solid support" as used here includes all polymeric materials onto which a nucleic acid fragment can be immobilized for use in diagnostic tests. Natural or synthetic materials, chemically modified or otherwise, can be used as solid support, especially polysaccharides such as cellulose materials, for example paper, cellulose derivatives such as cellulose acetate and nitrocellulose; polymers such as poly (vinyl) chloride, polyethylene, polystyrenes, polyamides, polyacrylates, polyurethanes, polycarbonates, polytetrachloroethylenes, copolymers such as vinyl chloride-propylene, vinyl chloride-vinyl acetate polymers, copolymers based on styrene or substituted derivatives of styrene, and synthetic fibres such as nylon.

The polymer material is especially a vinyl chloride/vinyl acetate, vinyl chloride/propylene copolymer, or a copolymer of styrene such as a butadiene-styrene copolymer; or a butadiene-styrene copolymer mixed with one or more polymers or copolymers chosen from polystyrene, styrene-acrylonitrile or styrene-methyl methacrylate copolymers, polypropylenes, polycarbonates or analogues. Advantageously, the solid support of the present invention is a polystyrene or a copolymer based on styrene comprising between about 10 and 90% by weight of styrene units.

The device according to the invention may be provided especially in the form of a microtitre plate, a sheet, a cone, a tube, a well, beads, particles, latex and the like.

The term "latex" designates an aqueous colloidal dispersion of any water-insoluble polymer.

The present invention requires the preparation of nucleic acid fragments conjugated to one or more hapten molecules via a covalent bond. This covalent bond can be established using direct or indirect approaches. These techniques make it possible to obtain a composite molecule modified in a perfectly known manner in relation to the position and degree of substitution.

By direct approach there is understood to mean the coupling by automated synthesis of the hapten added as a nucleotide during the synthesis, that is to say in the 5' and/or 3' position and in any other position in the chain. This requires the preparation of a derivative which can be used in automated synthesis, for example a phosphoramidite derivative, H-phosphonate or phosphotriester of the hapten or of a nucleotide substituted by the hapten on the base or on the glycosidic part. Likewise, the hapten can be introduced during the synthesis onto the internucleotide phosphorus atoms by oxidative phosphoramidation.

Two routes are envisaged for the indirect approaches:

The first requires, in a manner known per se, the introduction onto both partners, that is to say onto the nucleic acid fragment and onto the hapten respectively, of functional groups which are reactive with respect to each other. By way of example, a primary amine functional group carried by one of the partners will react with the N-hydroxysuccinimic ester of the other partner, likewise a thiol functional group will react with a maleimide, pyridyldisulphide or haloalkyl group and a phosphorothioate will react with a haloalkyl.

The second route involves the introduction onto the nucleic acid fragment and onto the hapten of functional groups having specific reactivities, but these functional groups are not directly reactive with respect to each other. The bond is established via a coupling agent.

The term coupling agent as used here designates a molecule containing at least two reactive ends or groups of the same nature or of different nature (homobifunctional or heterobifunctional coupling agent).

By way of example, a primary amine functional group and a carboxylic acid functional group can form an amide bond in the presence of a carbodiimide, two primary amine functional groups will be coupled in the presence of 1,4-phenylene diisothiocyanate or disuccinimidyl-suberate.

The reactive functional groups introduced onto the nucleic acid fragment can be chosen especially from amine, hydrazinoyl, hydrazonoyl, iminoyl, azidoyl, triazenoyl, triazanoyl, optionally substituted amide, semicarbazonoyl, aldehydyl, alkylthiol, arylthiol, carbamoyl, carboxyl, cyanoyl, haloalkyl, hydroxyl, N-hydroxysuccinimidyl, maleimide, phosphate, phosphorodithioate, phosphite, phosphonate, phosphorothioate, pyridyldisulphide, sulphamoyl and thiophosphate.

The reactive functional groups introduced (or optionally already present) on the hapten can be chosen, by way of example, from amine, hydrazinoyl, hydrazonoyl, iminoyl, azidoyl, triazenoyl, triazanoyl, optionally substituted amide, semicarbazonoyl, aldehydyl, alkylthiol, arylthiol, carbamoyl, carboxyl, cyanoyl, haloalkyl, hydroxyl, N-hydroxysuccinimidyl, maleimide, phosphate, phosphorodithioate, phosphite, phosphonate, phosphorothioate, pyridyldisulphide, sulphamoyl, thiophosphate groups.

The introduction of these reactive functional groups (and consequently the subsequent grafting of the hapten) on the nucleic acid fragments can be carried out at any position in the chain using for example reagents synthesized according to known or commercially available methods. By way of example, the modifications can be carried out at position 5' using an Aminolink II type reagent (Applied Biosystems ref. 400808); at position 3' using a solid phase such as that sold by the company Clontech Lab Inc under the reference 5221, or that described by Reed et al. (1991) Bioconjugate Chem., 2,217–225; on the nucleic bases (Glen Research ref. 101039); on the glycosidic part by modification of the glycosidic part using for example a ribofuranose substituted at position 2' in place of a 2'-deoxyribofuranose (Yamana et al. (1991) Tetrahedron Lett., 32, 6347–6350), or by substituting a nucleoside by an alkylamine compound (Clontech Lab Inc, ref. 5203) or alternatively by substitution of an internucleotide phosphate according to procedures described by Froehler et al., (1988) Nucl. Acids Res., 16, 11, 4831–4839.; Conway and McLaughlin (1991) Bioconjugate Chem., 2, 452–457; Letsinger et al. (1989) Proc. Natl. Acad. Sci. USA, 86,6553–6556.

Likewise, if necessary, the modification of the hapten for the introduction of a reactive, functional group can be carried out at any appropriate position in the hapten molecule. An example of modification is given in "Preparation of antigenic steroid-protein conjugate", F. Kohen et al., in Steroid immunoassay, Proceedings of the fifth tenovus workshop, Cardiff, April 1974, ed. EHD Cameron, S. H. Hillier, K. Griffiths.

The attachment of the nucleic acid fragment-hapten conjugate onto the solid phase can be carried out directly or indirectly.

Using the direct manner, two approaches are possible, either by adsorption of the conjugate onto the solid suppport, that is to say by non-covalent bonds (mainly of the hydrogen, Van der Walls or ionic type), or by establishing covalent bonds between the conjugate and the support.

Using the indirect manner, they can be attached beforehand (by adsorption or covalent bonding) onto the solid support an anti-conjugate compound capable of interacting with the nucleic acid fragment of the conjugate so as to immobilize the whole on the solid support.

By way of example, this anti-conjugate compound may be: an antinucleic acid fragment antibody such as that described by P. CROS et al. (monoclonal antibodies to alpha deoxyribonucleotides, (1993), NAMA conference, poster 4-37); a nucleic acid fragment having a sequence which is at least partially complementary to the nucleic acid fragment of the conjugate; a protein specifically binding the single-stranded nucleic acid fragment of the conjugate such as the single-stranded binding protein of E. coli or the protein encoded by gene 32 of bacteriophage T4; a ligand-receptor system, for example by grafting onto the nucleic acid fragment a molecule such as a vitamin and by immobilizing, on the solid phase, the corresponding receptor (for example the biotin-streptavidin system); a protein binding onto a specific sequence, commonly called promoter, such as the RNA polymerases and especially the phage RNA polymerases such as T7, T3, SP6 RNA polymerases.

The device according to the invention can be used for carrying out a competitive assay of haptens in a sample, especially a biological fluid, in which the immobilized reagent competes with the hapten in the sample for its binding to a specific antibody introduced in predetermined proportions. The presence of the specific antibody attached to the solid support is revealed by the usual methods. For example, the specific antibody is labelled with any appropriate marker, or the immune complex (immobilized hapten/anti-hapten antibody) attached onto the solid support, capable of being formed, is revealed using an anti-complex antibody labelled with any appropriate marker. Preferably, the anti-complex antibody is an antibody directed against the antibody of the complex formed.

The subject of the invention is also a process for assaying a hapten in a liquid sample characterized by the fact that:

a predetermined quantity of antibodies capable of recognizing the hapten is added to the sample;

the sample is brought into contact with the device as described above;

the quantity of antibody attached to the solid support is evaluated;

and the quantity of haptens present in the sample is deduced therefrom according to known methods.

This process is carried out according to techniques known per se. Of course the first two stages can be carried out in any order. The quantity of antibody attached is evaluated after an appropriate incubation time.

The quantity of hapten can for example be determined with the aid of a calibration curve obtained by calibrating the device with the aid of samples containing various known quantities of hapten, and which makes it possible to establish the correlation between the quantity of antibody attached and the corresponding quantity of haptens.

The device of the invention can also serve for assaying anti-hapten antibodies in a sample. For that, it is possible, according to a specific embodiment, to bring the sample into contact with the device and then to reveal, according to known methods, the possible presence of anti-hapten antibodies attached. The revealing can be carried out for example with the aid of labelled antibodies directed against the Fc fragment of the antibodies of the species from which the anti-hapten antibodies of interest are derived. According to another embodiment, the procedure can be carried out by a competitive method by adding to the sample a known quantity of labelled anti-hapten antibodies and by determining the quantity of labelled antibodies attached. By comparing with a calibration curve previously established, it is possible to deduce therefrom the quantity of anti-hapten antibodies originally present in the sample.

There will now be given, by way of an illustration, examples of preparation of the device according to the invention as well as examples for using the support. In these examples, the expression "speed vac" designates a rotary concentrator-lyophilizer.

DESCRIPTION OF PREFERRED EMBODIMENTS

EXAMPLE 1

Figure 1:
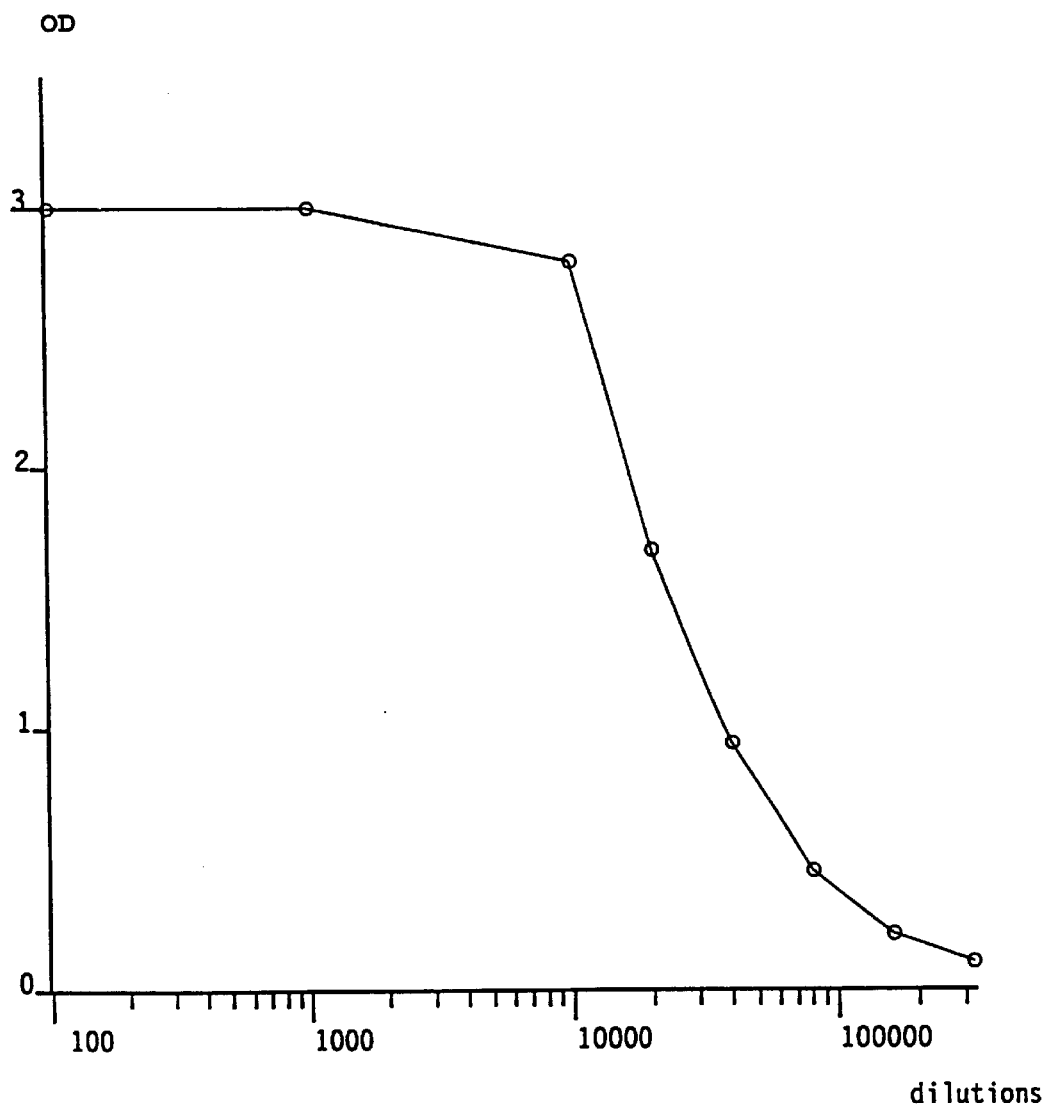
FIG. 1 shows a titration curve obtained in a competitive assay for estradiol.

Synthesis of oligonucleotides for the coupling onto hasten

The oligonucleotides are synthesized in an automated 394 apparatus from the company APPLIED BIOSYSTEMS using the chemistry of phosphoramidites according to the constructor's procedure. To allow the coupling of the oligonucleotide to a hapten at a well defined position, reactive functional groups are introduced onto the oligonucleotides by means of binding arms compatible with the automated synthesis. The arms used in the present invention and given here by way of example are described in Table 1.

The phosphoramidite arm referenced 1 is added to the 5' end of the oligonucleotide according to the standard automated synthesis procedure. The reactive functional group is at the 5 end of the oligonucleotide.

In the case of the compound having the reference 2, the reactive functional group is carried by the thymine base at position 5. This compound can be introduced at any position of the oligonucleotide except the 3' end.

In the case of the compound carrying the reference 3, the automated synthesis starts with silica grafted by the arm according to the standard procedure. The reactive functional group is at the 3' end of the oligonucleotide.

After deprotection overnight at 55° C. in 33% $NH_4OH$, followed by precipitation in ethanol at −20° C., the oligonucleotides are dried under vacuum and taken up in 1 ml of water.

In all cases the modified oligonucleotides are purified by reversed-phase high-pressure liquid chromatography (HPLC) on a Brownlee RP18 column (10 mm–25 cm).
Conditions:
Flowrate 4.6 ml/min,
Gradient: 10% to 35% of buffer B over 30 min, 35% to 100% of buffer B over 3 min.
The characteristics of buffers A and B are the following:
Buffer A: 0.1 molar triethylammonium acetate (TEAA) pH=7.00.
Buffer B: 50% buffer A+50% $CH_3CN$.

TABLE 2-continued

| 196 | 4 | alpha | 23.21 |
| 1803 | 5 | alpha | 20.04 |

SEQ ID No. 1:
ACTAAAAACT AGTAATGCAA AG  22
SEQ ID No. 2:
ATGTCACGAG CAATTAAGCG  20
SEQ ID No. 3:
ACTAAAAACT AGNAATGCAA AG  22
SEQ ID No. 4:
ACCCCGAGAT TTACGTTATG T  21
SEQ ID No. 5:
TTTTTTTTTT TTTTTTTTTT  20

(*) the beta nucleotides are natural nucleotides (the glycosidic bond is in the beta anomeric form). As regards the alpha nucleotides, the glycosidic bond is in the alpha anomeric form. The oligonucleotides containing the alpha nucleotides were prepared according to the technique described in Patent Application PCT WO 88/04 301.
(**) Tr represents the retention time in minutes (min) for the oligonucleotide under the following conditions:
Brownlee RP18 column: (4.6 mm–25 cm)
Conditions: flowrate 1 ml/min,
Gradient: 10% to 35% of buffer B over 30 min, 35% to 100% of buffer B over 3 min.

TABLE 1

| No. | Formula | Supplier | Ref. |
|---|---|---|---|
| 1 | $CF_3-CNH(CH_2)_6-OP(OCH_3)(N(IsoPr)_2)$ with C=O | Applied Biosystems | 400808 |
| 2 | [Structure: DMTrO-sugar with base having 5-substituent: CH=CH-C(=O)-NH(CH_2)_6-NHCCF_3, and 3'-O-P(O(CH_2)_2-CN)(N(IsoPr)_2)] | GlenResearch | 101039 |
| 3 | CPG-LCAA-O—CH(CH_2NHFmoc)—CH_2-ODMTr | Clontech Lab Inc | 5221-1 |

DMTr = dimethoxytrityl
Fmoc = 9-fluorenylmethoxycarbonyl
CPG = controlled porosity glass beads
LCAA = long chain alkyl amine (spacer arm)

The oligonucleotides modified by the arms in Table 1 and which are used in the present invention are described in Table 2.

TABLE 2

| Customary number for the oligonucleotide | SEQ ID No. | Nucleotide (*) | Tr (**) |
|---|---|---|---|
| 57 | 1 | beta | 19.54 |
| 319 | 2 | beta | 18.45 |
| 1257 | 3 | beta | 19.85 |

The characteristics of buffers A and B are the following:

Buffer A: 0.1 molar triethylammonium acetate (TEAA) pH=7.00
Buffer B: 50% buffer A+50% $CH_3CN$.

Coupling of a hapten to an oligonucleotide

The haptens used in the present invention and given here by way of example are described in Table 3.

TABLE 3

| HAPTEN TO BE ASSAYED | ACTIVATED HAPTEN USED FOR THE COUPLING | SUPPLIER | REFERENCE |
|---|---|---|---|
| ESTRADIOL | ESTRADIOL-6-CARBOXYMETHOXIME-N-HYDROXYSUCCINIMIDE ESTER | BOEHRINGER MANNHEIM | 05.21041 |
| TETRAIODO-THYRONINE T4 | N-BOC-THYROXINE-N-HYDROXY-SUCCINIMIDE ESTER | BOEHRINGER MANNHEIM | 05.21003 |
| TRIIODOTHYRONINE T3 | N-BOC-TRIIODOTHYRONINE-N-HYDROXYSUCCINIMIDE ESTER | BOEHRINGER MANNHEIM | 05.21002 |
| TESTOSTERONE | TESTOSTERONE-19-HEMISUCCINATE-N-HYDROXYSUCCINIMIDE ESTER (*) | BIOMERIEUX | / |

(*) Derivative of 19-hydroxytestosterone.

The hapten testosterone, provided by BIOMERIEUX, is prepared according to the method described in J. Steroid Biochem., 23(6a), pages 981–989, 1985 by A. WHITE et al.

50 nmol of oligonucleotides are dried in a speed vac and taken up in 20 µl of 0.1M sodium borate buffer, pH 9.3. 300 µl of an activated hapten solution (5 mg/ml in DMF) are added dropwise and then left stirring for 3 hours at 50° C. After centrifugation, the supernatant is separated, the precipitate resulting from the centrifugation is taken up in 100 µl of water and then added to the supernatant. The mixture is treated with 250 µl of 3M sodium acetate pH 5.2 and then 5 ml of cold ethanol (−20° C.). After 30 minutes at −80° C. and centrifugation, the pellet is taken up in 500 µl of water.

The oligonucleotide-hapten conjugate is purified by HPLC under the following conditions:
BECKMAN ODS column (10 mm–25 cm).
Conditions: flowrate 4.6 ml/min,
Gradient: 20% to 30% of buffer B over 10 min, 30% to 70% of buffer B over 20 min.
The characteristics of buffers A and B are the following:
Buffer A: 0.1 molar triethylammonium acetate (TEAA) pH=7.00
Buffer B: 50% buffer A+50% $CH_3CN$.

The peak corresponding to the coupling is dried in a speed vac and then taken up in 500 µl of water.

The various oligonucleotide-hapten conjugates prepared in the present invention are summarized in Table 4.

TABLE 4

| Oligonucloetide-hapten conjugate | Oligonucleotide | Hapten (*) | Tr (**) |
|---|---|---|---|
| A | 57 | ESTRADIOL | 16.18 |
| B | 57 | T3 | 27.44 |
| C | 57 | T4 | 25.79 |
| D | 57 | TESTOSTERONE | 27.96 (a) |
| E | 319 | ESTRADIOL | 14.50 |
| F | 1257 | T4 | 22.71 |
| G | 196 | ESTRADIOL | 15.65 |
| H | 1803 | ESTRADIOL | 15.45 |

(*) see Table 3 for the exact formula of the hapten used for the coupling.
(**) Tr is the retention time for the purified product under the following conditions:
Brownlee RP 300 column (4.6 mm x 100 mm)
Flowrate: 1.0 ml/min
Gradient: 20% to 30% of buffer B over 10 min, 30% to 70% of buffer B over 20 min.
(a) for conjugate D, the gradient is 10 to 40% of B in 30 min.

The characteristics of buffers A and B are the following:
Buffer A: 0.1 molar triethylammonium acetate (TEAA) pH=7.00.
Buffer B: 50% buffer A+50% $CH_3CN$.

EXAMPLE 2

Use of an oligonucleotide-estradiol conjugate immobilized by direct adsorption on a solid support, for the determination of estradiol by the competitive type immunoenzymatic technique An anti-estradiol monoclonal antibody (BIOMERIEUX ref. 10G6E9H4C1D6) obtained by the conventional technique described by G. Köhler and C. Milstein (Nature 256. 495–497 (1975)) purified from ascitic fluids by ABx ion-exchange type chromatography (Baker-72 69 00), and then conjugated to peroxidase (marketed by the company FORDRAS) according to the technique described in 1974 by Nakane P. K. and Kawoi A. (J. Histochem. Cytochem, 22: 1084) is used in a determined non-saturating concentration established from a titration curve. The titration curve is obtained as follows: in a well of a Maxisorb NUNC polystyrene plate (marketed by the company Polylabo Paul Block under the reference 4-39454), the conjugate A obtained as described in Example 1 is immobilized at the rate of 100 µl per well and at a concentration of 0.15 µM in 3X PBS buffer (0.45M NaCl; 0.15M sodium phosphate; pH 7.0). This plate is incubated overnight at 22° C. or for 1 hour at a temperature of 37° C. The plate is washed three times with 300 µl of PBS buffer—0.05% Tween (0.15M NaCl; 0.05M sodium phosphate; pH 7.0; Tween 20 at a final concentration of 0.05% (Tween: trade name)). The sites in the plate which are not occupied by the oligonucleotide-hapten conjugate A are saturated by the addition of 100 µl of a PBS-milk solution at a final concentration of 1% (0.15M NaCl; 0.05M sodium phosphate; pH 7.0; 1% Regilait skimmed milk). The plate is incubated for 1 hour at 37° C. and then rinsed 3 times with 300 µl of PBS buffer—0.05% Tween. Into each well of the plate are added 100 µl of serial dilutions of the labelled anti-estradiol antibody in PBS buffer, and incubated for 15 minutes with stirring at 22° C. The plate is rinsed three times with PBS buffer—0.05% Tween, then once with distilled water. 100 µl of OPD (Ortho-phenylene-diamine, marketed by the company Cambridge Medical Biotechnology under the reference 456) substrate at the concentration of 4 mg/ml in an OPD buffer (0.05M citric acid, 0.1M $NaH_2PO_4$; pH 4.93) to which is added immediately before use $H_2O_2$ at 30 volumes diluted 1/1000, are introduced into the wells of the plate. The enzymatic reaction is blocked by the addition of 100 µl of 1N $H_2SO_4$ after incubating for 30 minutes at 37° C. The reading is carried out at 492 nm in a Biowhittaker Microplate 2001 reader. The titration curve obtained is represented in FIG. 1; each point represents the mean of two values minus the value for the non-specific attachment. From this titration curve, the labelled anti-estradiol antibody, which will be subsequently used, is chosen at a determined dilution corresponding to a non-saturating enzymatic activity, so as to give an OD of 1.5 at 492 nm.

The determination of the estradiol molecule to be assayed is carried out according to the same procedure as that described above, except for the stage for adding the labelled anti-estradiol antibody. At this stage, 50 µl of anti-estradiol antibody at the dilution previously determined are previously mixed with 50 µl of a solution chosen from solutions with increasing estradiol concentration. The results are represented in Table 5 below.

TABLE 5

| Estradiol concentration pg/ml (*) | OD 492 nm (**) |
|---|---|
| 0 | 1.441 |
| 0.1 | 1.379 |
| 1 | 1.416 |
| 10 | 1.254 |
| 100 | 0.274 |
| 1000 | 0.019 |

* The samples containing the various estradiol concentrations are prepared by adding known quantities of estradiol (17beta-estradiol marketed by the company Sigma under the reference E 1631) in PBS buffer.
** Each point represents the mean OD of two values minus the value for the non-specific attachment (reading 492 nm).

The results from the calibration series presented in Table 5 show a good inhibition of the attachment of the labelled antibody when the estradiol concentration increases.

EXAMPLE 3

Figure 2:
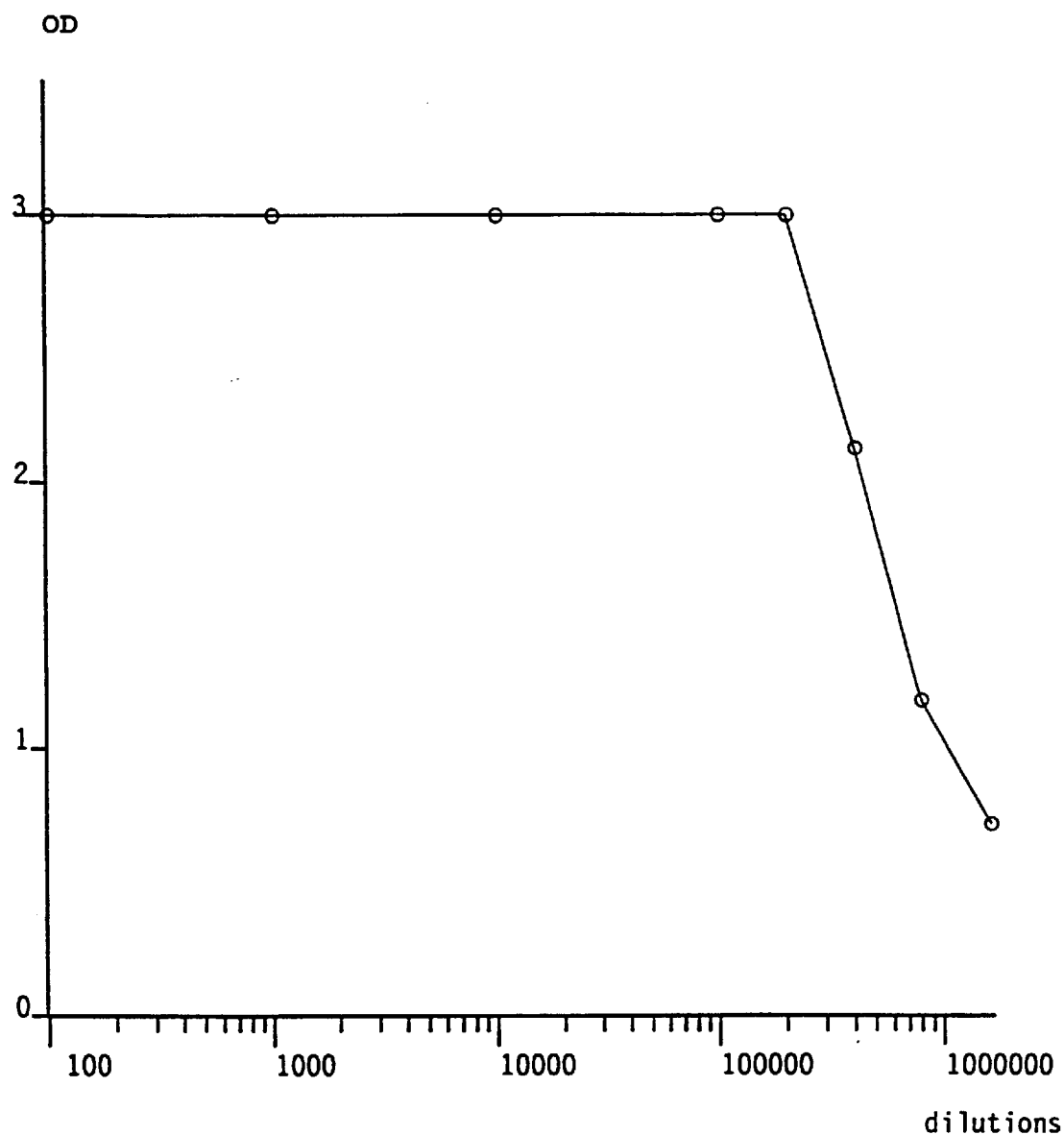
FIG. 2 shows a titration curve obtained in a competitive assay for testosterone.

Use of an oligonucleotide-testosterone conjugate immobilized by direct adsorption on a solid support, for the determination of testosterone by the competitive type immunoenzymatic technique An anti-testosterone rabbit polyclonal serum (marketed by the company Biospacific under the reference 052B4089) is used at a determined non-saturating concentration established from a titration curve. The titration curve is obtained as follows:

In the wells of a Maxisorb NUNC polystyrene plate (marketed by the company Polyabo Paul Block under the reference 4-39454), the oligonucleotide hapten conjugate D obtained as described in Example 1 is immobilized at the rate of 100 µl per well and at a concentration of 0.15 µM in 3X PBS buffer (0.45M NaCl; 0.15M sodium phosphate; pH 7.0). This plate is incubated overnight at 22° C. or for 1 hour at a temperature of 37° C. The plate is washed three times with 300 µl of PBS buffer—0.05% Tween (0.15M NaCl; 0.05M sodium phosphate; pH 7.0; Tween 20 at a final concentration of 0.05% (Tween: trade name)). The sites in the plate which are not occupied by the oligonucleotide-hapten conjugate D are saturated by the addition of 100 µl of a PBS-milk solution at a final concentration of 1% (0.15M NaCl; 0.05M sodium phosphate; pH 7.0; 1% Regilait skimmed milk). The plate is incubated for 1 hour at 37° C. and then rinsed 3 times with 300 µl of PBS buffer—0.05% Tween. Into each well of the plate are added 100 µl of serial dilutions of rabbit anti-testosterone serum in PBS buffer, and incubated for 15 minutes with stirring at 22° C. The plate is rinsed three times with 300 µl of PBS buffer—0.05% Tween, then 100 µl of a goat polyclonal antibody antirabbit IgG Fc labelled with alkaline phosphatase (marketed by the company Jackson Immunoresearch Laboratories under the reference 111-055-046) diluted 1/1000 in PBS buffer are incorporated into the wells of the plate. The latter is incubated for one hour at 37° C. and is then rinsed three times with PBS buffer—0.05% Tween, then once with distilled water. 100 µl of PNPP (para-nitrophenyl phosphate marketed by the company Sigma under the reference 104-0) at the concentration of 2 mg/ml in diethanolamine-HCl buffer (1.29M diethanolamine; 0.56 mM MgSO$_4$; 0.38 mM NaN$_3$; 0.012N ECl; pH 9.8) substrate are added into the wells of the plate. The enzymatic reaction is blocked by the addition of 100 µl of 1N NaOH after incubating for 30 minutes at 37° C. The reading is carried out at 405 nm in a Biowhittaker Microplate 2001 reader. The titration curve obtained is represented in FIG. 2; each point represents the mean of two values minus the value for the non-specific attachment. From this titration curve, the anti-testosterone antibody, which will be subsequently used, is chosen at a determined dilution corresponding to a non-saturating enzymatic activity, so as to give an OD of 1.5 at 405 nm.

The determination of the testosterone molecule to be assayed is carried out according to the same procedure as that described above, except for the stage for adding the anti-testosterone antibody. At this stage, 50 µl of anti-testosterone antibody at the dilution previously determined are previously mixed with 50 µl of a solution chosen from solutions with increasing testosterone concentration. The results are represented in Table 6 below.

TABLE 6

| Testosterone concentration pg/ml (*) | OD 405 nm (**) |
|---|---|
| 0 | 2.607 |
| 10 | 2.392 |
| 100 | 1.293 |
| 1000 | 0.467 |
| 10000 | 0.203 |

* The samples containing the various testosterone concentrations are prepared by adding known quantities of testosterone (4-androsten-17-ol-3-one marketed by the company Sigma under the reference T 1500) in PBS buffer.
** Each point represents the mean OD of two values minus the value for the non-specific attachment (reading 405 nm).

The results from the calibration series presented in Table 6 show a good inhibition of the attachment of the specific antibody when the testosterone concentration increases.

EXAMPLE 4

Use of an oligonucleotide-estradiol conjugate immobilized by means of a complementary oligonucleotide on a solid support for the determination of estradiol by the competitive type immunoenzymatic technique The anti-estradiol monoclonal antibody used is identical to that described in Example 2 (BIOMERIEUX ref. 10G6E9H4C1D6).

The titration curve is obtained in accordance with the procedure described in Example 2, except for the first stage which proceeds as follows:

In the wells of a Maxisorb NUNC microtitre plate is immobilized an oligonucleotide of a sequence complementary to the nucleotide sequence of oligonucleotide 57 (sequence ID No. 1) described in Example I at the rate of 100 µl per well and at a final concentration of 0.75 µM in 3X PBS buffer. The plates are incubated overnight at 22° C. or for one hour at a temperature of 37° C. The plate is washed 3 times with 300 µl of PBS buffer—0.05% Tween. The sites of the plate which are not occupied by this oligonucleotide are saturated by the addition of 100 µl of a PBS-milk solution at a final concentration of 1%. The plate is incubated for 1 hour at 37° C. and then rinsed 3 times with 300 µl of PBS buffer—0.05% Tween. Into each well are added 100 µl of the oligonucleotide-hapten conjugate A obtained as described in Example 1 at a concentration of 0.15 µM, either in 3X PBS buffer or in PEG buffer (0.1M NaH$_2$ PO$_4$/Na$_2$ HPO$_4$; 0.5M NaCl; pH 7.0, 0.05% Tween 20; 0.14 mg/ml of salmon sperm DNA; 2% PEG 4000) for 1 hour at 37° C. The plate is washed 3 times with 300 µl of PBS buffer—0.05% Tween.

The rest of the experiment proceeds in accordance with the procedure described in Example 2.

Figure 3:
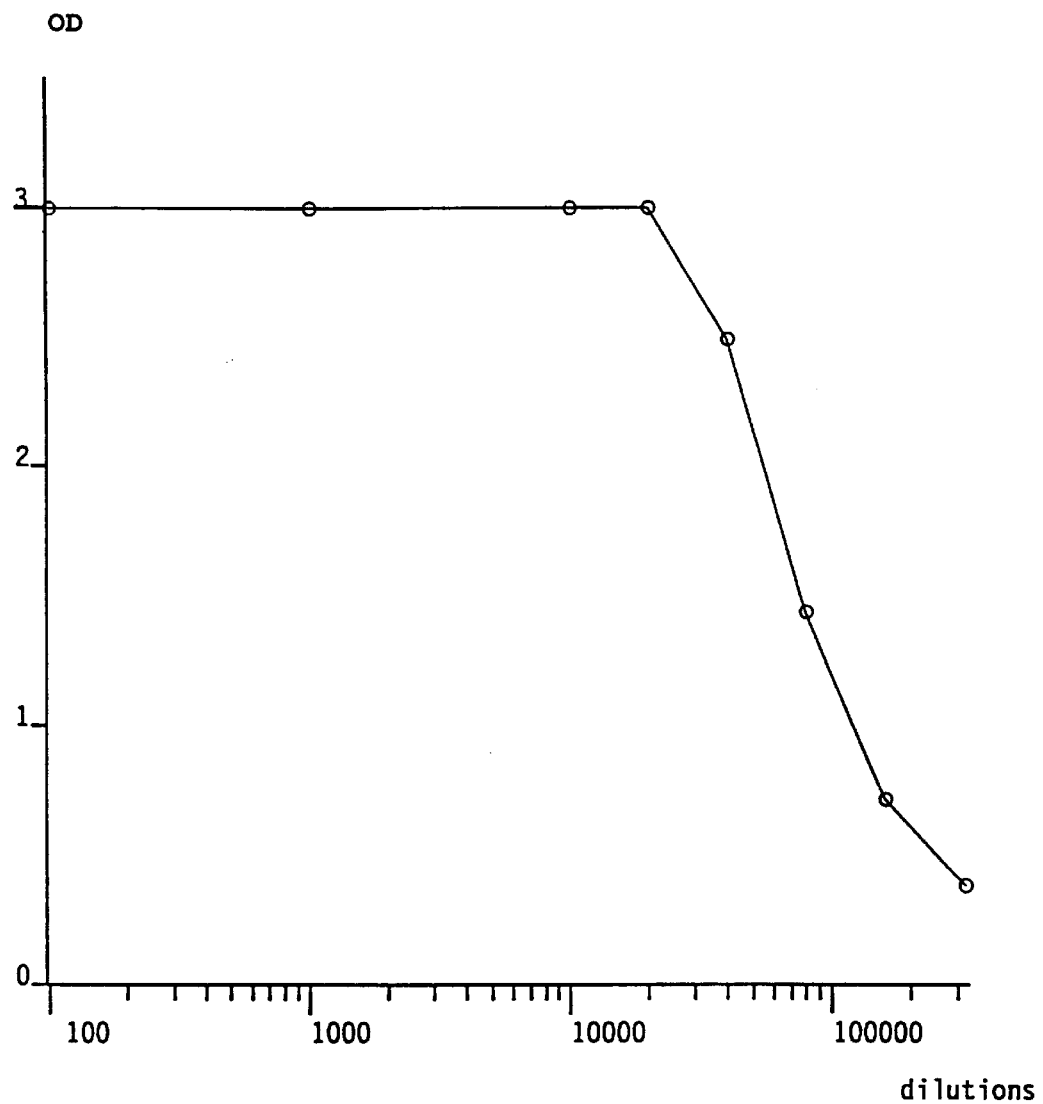
FIGS. 3 and 4 show titration curves obtained for a competitive assay for estradiol wherein immobilization is accomplished by means of a complementary oligonucleotide on a solid support.
Figure 4:
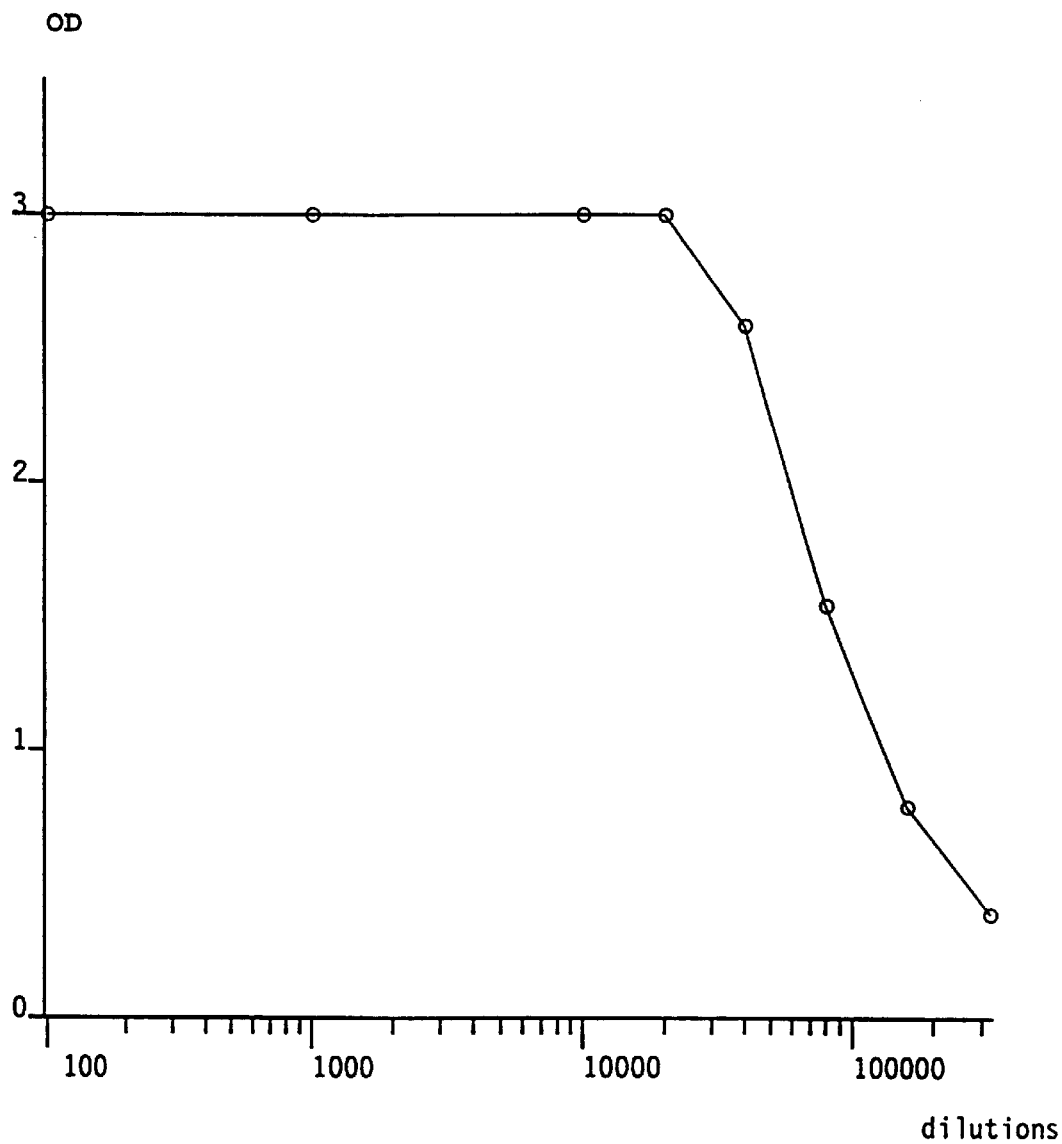

The titration curves obtained are respectively represented in FIGS. 3 (3X PBS buffer) and 4 (PEG buffer). The labelled antibody, which will be subsequently used, is chosen at a determined dilution corresponding to a non-saturating enzymatic activity so as to give an OD of 1.5 read at 492 nm.

The determination of the estradiol molecule to be assayed is carried out according to the methods described in Example 2.

The results obtained are presented respectively in Tables 7 (3X PBS buffer) and 8 (PEG buffer) below.

TABLE 7

| Estradiol concentration pg/ml (*) | OD 492 nm (**) |
|---|---|
| 0 | 1.875 |
| 0.1 | 1.815 |
| 1 | 1.823 |
| 10 | 1.428 |
| 100 | 0.391 |
| 1000 | 0.053 |

TABLE 8

| Estradiol concentration pg/ml (*) | OD 492 nm (**) |
|---|---|
| 0 | 1.859 |
| 0.1 | 1.827 |
| 1 | 1.730 |
| 10 | 1.512 |
| 100 | 0.362 |
| 1000 | 0.058 |

* The samples containing the various estradiol concentrations are prepared by adding known quantities of estradiol (17beta-estradiol marketed by the company Sigma under the reference E 1631) in PBS buffer.
** Each point represents the mean OD of two values minus the value for the non-specific attachment (reading 492 nm).

The results for the calibration series presented in Tables 7 and 8 show a good inhibition of the attachment of the labelled antibody when the estradiol concentration increases.

EXAMPLE 5

Use of an oligonucleotide-estradiol conjugate immobilized by means of an anti-oligonucleotide monoclonal antibody on a solid support, for the determination of estradiol by the competitive type immuno-enzymatic technique The anti-estradiol monoclonal antibody used is identical to that described in Example 2 (BIOMERIEUX ref. 10G6E9H4C1D6).

The titration curve is obtained in accordance with the procedure described in Example 2 except for the first stage which proceeds as follows:

An anti-oligonucleotide monoclonal antibody (BIOMERIEUX reference 3H11H10) obtained by the conventional technique described by G. Köhler and C. Milstein and purified from ascitic fluids, by ABx ion-exchange type chromatography (Baker—72 6900), is immobilized in a Maxisorb NUNC microtitre plate at the rate of 100 µl per well at a concentration of 10 µg per ml, in bicarbonate buffer (0.05M NaHCO$_3$; pH 9.6). The plate is incubated overnight at 22° C. or for 1 hour at 37° C.

The plate is washed three times with 300 µl of PBS buffer—0.05% Tween [0.15M NaCl; 0.05M sodium phosphate; pH 7.0; Tween 20 at a final concentration of 0.05% (Tween: trade name)]. The sites in the plate which are not occupied by the anti-oligonucleotide monoclonal antibody are saturated by the addition of 100 µl of a PBS-milk solution at a final concentration of 1% (0.15M NaCl; 0.05M sodium phosphate; pH 7.0; 1% Regilait skimmed milk). The plate is incubated for one hour at 37° C. and then rinsed 3 times with 300 µl of PBS buffer—0.05% Tween.

To each well are added 100 µl of oligonucleotide-hapten conjugate G as described in Example 1 at a concentration of 0.15 µM in PBS buffer, for 1 hour at 37° C. The plate is washed 3 times with 300 µl of PBS buffer—0.05% Tween.

The rest of the experiment proceeds in accordance with the procedure described in Example 2.

Figure 5:
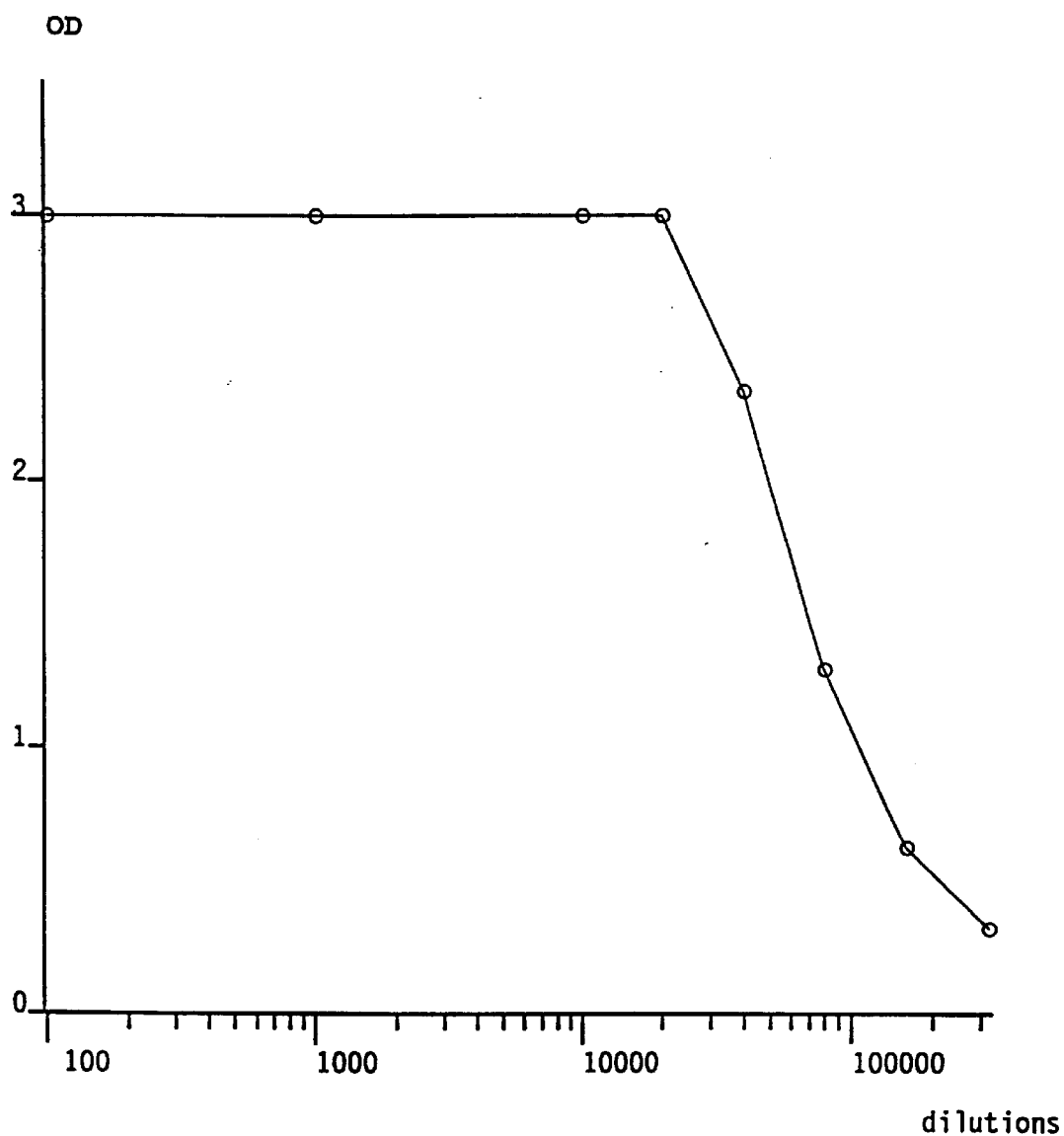
FIGS. 5 and 6 show titration curves for a competitive assay of estradiol wherein immobilization is accomplished by using an anti-oligonucleotide monoclonal antibody.

The titration curve obtained is represented in the accompanying FIG. 5. The labelled antibody, which will be subsequently used, is chosen at a determined dilution corresponding to a non-saturating enzymatic activity, so as to give an OD of 1.5 at 492 nm.

The determination of the estradiol molecule to be assayed is read out according to the methods described in Example 2.

The results obtained are presented in Table 9 below.

TABLE 9

| Estradiol concentration pg/ml (*) | OD 492 nm (**) |
|---|---|
| 0 | 2.084 |
| 0.1 | 2.028 |
| 1 | 2.061 |
| 10 | 1.810 |
| 100 | 0.452 |
| 1000 | 0.056 |

* The samples containing the various estradiol concentrations are prepared by adding known quantities of estradiol (17beta-estradiol marketed by the company Sigma under the reference E 1631) in PBS buffer.
** Each point represents the mean OD of two values minus the value for the non-specific attachment (reading 492 nm).

The results for the calibration series presented in Table 9 show a good inhibition of the attachment of the labelled antibody when the estradiol concentration increases.

EXAMPLE 6

Use of an oligonucleotide-estradiol conjugate immobilized by means of an anti-oligonucleotide monoclonal antibody on a solid support, for the determination of estradiol by the competitive type immunoenzymatic technique The experimental conditions are identical to those described in Example 5 except for the use of the oligonucleotide-hapten conjugate H and an antibody directed against the oligonucleotide 1803 (BIO MERIEUX Ref. 3H11H10).

Figure 6:
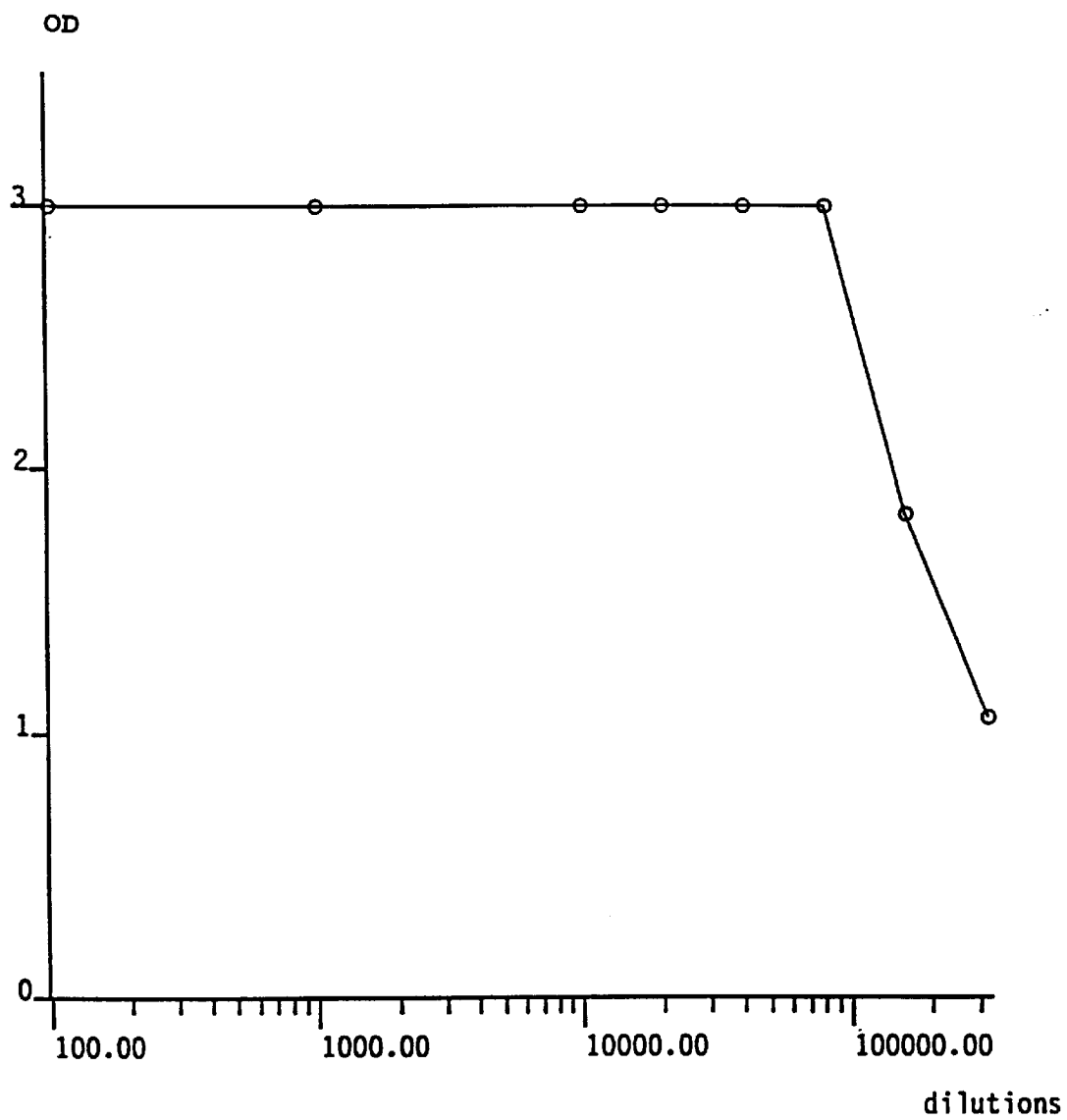

The titration curve obtained is represented in the accompanying FIG. 6. The labelled antibody, which will be subsequently used, is chosen at a determined dilution corresponding to a non-saturating enzymatic activity, so as to give an OD of 1.5 at 492 nm.

The determination of the estradiol molecule to be assayed is carried out according to the methods described in Example 2.

The results obtained are presented in Table 10 below.

TABLE 10

| Estradiol concentration pg/ml (*) | OD 492 nm (**) |
|---|---|
| 0 | 0.973 |
| 1 | 0.934 |
| 10 | 0.628 |

TABLE 10-continued

| Estradiol concentration pg/ml (*) | OD 492 nm (**) |
|---|---|
| 100 | 0.110 |
| 1000 | 0.017 |

\* The samples containing the various estradiol concentrations are prepared by adding known quantities of estradiol (17beta-estradiol marketed by the company Sigma under the reference E 1631) in PBS buffer.
\*\* Each point represents the mean OD of two values minus the value for the non-specific attachment (reading 492 nm).

The results for the calibration series presented 492 nm).

The results for the calibration series presented in Table 10 show a good inhibition of the attachment of the labelled antibody when the estradiol concentration increases.

---

We claim:

1. Hapten assay device for assaying a first hapten comprising a solid support and a reagent covalently linked to a nucleic acid fragment to form a conjugate immobilized or immobilizable on said solid support by means of said fragment, wherein said reagent is a second hapten that competes with said first hapten for specific binding to antibodies that bind to said first hapten.

2. Device according to claim 1, wherein said conjugate is immobilized by passive adsorption of said fragment onto the solid support.

3. Device according to claim 1, wherein said conjugate is immobilized by covalent coupling of said fragment onto the solid support.

4. Device according to claim 1, wherein said conjugate is immobilized onto the solid support by hybridization with a second nucleic acid fragment hybridizable with said nucleic acid fragment of said conjugate, said second nucleic acid fragment being immobilized on the support.

5. Device according to claim 1, wherein said conjugate is immobilized on the support by an antibody or an antibody fragment directed against said nucleic acid fragment of said conjugate, said antibody or antibody fragment being immobilized on said solid support.

6. Device according to claim 1, wherein said device comprises a protein immobilized on the support said protein having an affinity for binding with said fragment.

7. Device according to claim 1, wherein the nucleic acid fragment is selected from the group consisting of a DNA fragment and an RNA fragment.

8. Device according to claim 7, wherein said nucleic acid fragment is a deoxyribonucleotide, a ribonucleotide, a deoxyribonucleoside or a ribonucleoside.

9. Device according to claim 7, wherein the nucleic acid fragment is an oligodeoxyribonucleotide or an oligoribonucleotide with a length of between 2 and 100 nucleotides.

10. Device according to claim 9, wherein the length is between 10 and 50 nucleotides.

11. Device according to claim 7, wherein the nucleic acid fragment comprises a naturally modified base.

12. Device according to claim 11, wherein the naturally modified base is selected from the group consisting of 6-ketopurine, xanthine, 5-methyl-cytosine and 2-aminopurine.

13. Device according to claim 7, wherein the nucleic acid fragment comprises an unnatural modified base.

14. Device according to claim 7, wherein the unnatural modified base is selected from the group consisting of thioguanine and 8-oxoguanine.

15. Device according to claim 13, wherein the nucleic acid fragment is modified on a glycosidic portion.

16. Device according to claim 7, wherein the nucleic acid fragment is modified in a phosphodiester skeleton.

17. Device according to claim 7, wherein the nucleic acid fragment comprises nucleosides that are each alpha or each beta anomers.

18. Device according to claim 7, wherein nucleosides of the nucleic acid fragment are selected from the group consisting of D-nucleosides and L-nucleosides.

19. Device according to claim 11, wherein said second hapten is identical to said first hapten.

20. Process for assaying a first hapten in a liquid sample comprising:
   adding to said sample a predetermined quantity of antibodies to which said first hapten specifically binds;
   contacting the sample with the device as defined in claim 1;
   evaluating the quantity of antibody attached to the solid support of the device; and
   deducing the quantity of first hapten present in the sample.

21. Process according to claim 20, wherein said conjugate is immobilized by passive adsorption of said fragment onto the solid support.

22. Process according to claim 20, wherein said conjugate is immobilized by covalent coupling of said fragment onto the solid support.

23. Process according to claim 20, wherein said conjugate is immobilized onto the solid support by hybridization with a second nucleic acid fragment hybridizable with said nucleic acid fragment of the said conjugate, said second nucleic acid fragment being immobilized on the support.

24. Process according to claim 20, wherein said conjugate is immobilized on the support by an antibody or an antibody fragment directed against said nucleic acid fragment of said conjugate, said antibody or antibody fragment being immobilized on said solid support.

25. Process according to claim 20, wherein said device comprises a protein immobilized on the support by said fragment, said protein having an affinity for binding with said fragment.

26. Process according to claim 20, wherein the nucleic acid fragment is selected from the group consisting of a DNA fragment and an RNA fragment.

27. Process according to claim 20, wherein said nucleic acid fragment is a deoxyribonucleotide, a ribonucleotide, a deoxyribonucleoside or a ribonucleoside.

28. Process according to claim 20, wherein the nucleic acid fragment is an oligodeoxyribonucleotide or an oligoribonucleoside with a length of between 2 and 100 nucleotides.

29. Process according to claim 28, wherein the length is between 10 and 50 nucleotides.

30. Process according to claim 20, wherein the nucleic acid fragment comprises a naturally modified base.

31. Process according to claim 30, wherein the naturally modified base is selected from the group consisting of 6-ketopurine, xanthine, 5-methyl-cytosine and 2-aminopurine.

32. Process according to claim 20, wherein the nucleic acid fragment comprises an unnatural modified base.

33. Process according to claim 32, wherein the unnatural modified base is selected from the group consisting of thioguanine and 8-oxoguanine.

34. Process according to claim 20, wherein the nucleic acid fragment is modified on a glycosidic portion.

35. Process according to claim 20, wherein the nucleic acid fragment is modified in a phosphodiester skeleton.

36. Process according to claim 20, wherein the nucleic acid fragment comprises nucleosides that are each alpha or each beta anomers.

37. Process according to claim 20, wherein nucleosides of the nucleic acid fragment are selected from the group consisting of D-nucleosides and L-nucleosides.

38. Hapten assay device for assaying a first hapten consisting essentially of a solid support and a reagent covalently linked to a nucleic acid fragment to form a conjugate immobilized or immobilizable on said solid support by means of said fragment, wherein said reagent is a second hapten that competes with said first hapten for specific binding to antibodies that bind to said first hapten.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( i x ) FEATURE:
        ( D ) OTHER INFORMATION: alkylamine arm (product referenced 1 in Table 1) at the 5'end.

( x i ) SEQUENCE DESCRIPTION: SEQ ID NO:1:

A C T A A A A A C T   A G T A A T G C A A   A G           2 2

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( i x ) FEATURE:
        ( D ) OTHER INFORMATION: arm derived from aminopropanediol (product referenced 3 in Table 1) at the 3'end.

( x i ) SEQUENCE DESCRIPTION: SEQ ID NO:2:

A T G T C A C G A G   C A A T T A A G C G           2 0

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear -continued (ii) MOLECULE TYPE: other nucleic acid
    (A) DESCRIPTION: /desc = "SYNTHETIC DNA"

(ix) FEATURE:
    (D) OTHER INFORMATION: N represents a thymidine nucleoside
        (product referenced 2 in Table 1) having an alkylamine
        arm in position 5.

(xi) SEQUENCE DESCRIPTION: SEQ ID NO:3:

ACTAAAAACT AGNAATGCAA AG                                              22

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(ix) FEATURE:
        (D) OTHER INFORMATION: consists of nucleosides with an alpha
            anomer and carries an alkylamine arm (product referenced
            1 in Table 1) at the 5'end.

(xi) SEQUENCE DESCRIPTION: SEQ ID NO:4:

ACCCCGAGAT TTACGTTATG T                                               21

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(ix) FEATURE:
        (D) OTHER INFORMATION: consists of nucleosides with an alpha
            anomer and carries an arm derived from aminopropanediol
            (product referenced 3 in Table 1) at the 3'end.

(xi) SEQUENCE DESCRIPTION: SEQ ID NO:5:

TTTTTTTTT TTTTTTTTT                                                   20